(12) United States Patent
Weinstock et al.

(10) Patent No.: US 9,072,749 B2
(45) Date of Patent: Jul. 7, 2015

(54) TREATMENT OF AGE-RELATED MACULAR DEGENERATION

(76) Inventors: Joseph Weinstock, Wayne, PA (US); Sarah Jane Paikowsky, Scottsdale, AZ (US)

( * ) Notice: Subject to any disclaimer, the term of this patent is extended or adjusted under 35 U.S.C. 154(b) by 1425 days.

(21) Appl. No.: 12/602,323

(22) Filed: Nov. 30, 2009

(65) Prior Publication Data
US 2010/0316731 A1 Dec. 16, 2010

Related U.S. Application Data

(63) Continuation-in-part of application No. PCT/US2008/065212, filed on May 30, 2008.

(60) Provisional application No. 60/941,106, filed on May 31, 2007, provisional application No. 60/968,195, filed on Aug. 27, 2007.

(51) Int. Cl.
*A61K 31/55* (2006.01)
*C07D 223/16* (2006.01)

(52) U.S. Cl.
CPC .................................... *A61K 31/55* (2013.01)

(58) Field of Classification Search
CPC .............................. A61K 31/55; C07D 223/16
USPC ..................................... 540/595; 514/217.02
See application file for complete search history.

(56) References Cited

U.S. PATENT DOCUMENTS

| 4,197,297 | A | 4/1980 | Weinstock |
| 4,861,771 | A | 8/1989 | Gaitanopoulos et al. |
| 6,238,693 | B1 | 5/2001 | Luther et al. |
| 6,699,497 | B1 | 3/2004 | van Osdol et al. |
| 6,960,353 | B2 | 11/2005 | van Osdol et al. |
| 2003/0158162 | A1 | 8/2003 | Aiken |

FOREIGN PATENT DOCUMENTS

| CH | 637383 A5 | 7/1983 |
| EP | 0 022 330 A2 | 1/1981 |
| WO | 2004103263 A2 | 12/2004 |
| WO | 2007029008 A2 | 3/2007 |
| WO | 2008042399 A2 | 4/2008 |

OTHER PUBLICATIONS

Age-Related Eye Disease Study Research Group: "A Randomized, Placebo-Controlled, Clinical Trial of High-Dose Supplementation with Vitamins C and E, Beta Carotene and Zinc for Age-Related Macular Degeneration and Vision Loss", Archives of Ophthalmology, 119: 1417-1436 (2001).
H. Reitsamer et al., "Dopaminergic Vasodilation in the Choroidal Circulation by D1/D5 Receptor Activation", Investigative Ophthalmology & visual Science, 45(3): 900-905 (2004).
K. Huemer et al., "Effects of dopamine on retinal and choroidal blood flow parameters in humans", Br. J. Ophthalmol., 91: 1194-1198 (2007).

B. Xuan et al., "Improvement of Ocular Blood Flow and Retinal Functions with Puerarin Analogs", Journal of Ocular Pharmacology and Therapeutics, 15(3): 207-216 (1999).
B. Xuan et al., "Effects of Crocin Analogs on Ocular Blood Flow and Retinal Function", Journal of Ocular Pharmacology and Therapeutics, Mary Ann Liebert, Inc., New York, NY, vol. 15, No. 2, pp. 143-152 (1999).
S. Avetisov et al., "Effect of vasoactive agents on visual functions an ocular blood flow in patients with early manifestations of age-related macular degeneration", Vestnik Oftalmologii, 123(3): 26-28 (2007) [English Abstract on p. 28].
Gehrs, Karen M. et al., "Age-related macular degeneration-emerging pathogenetic and therapeutic concepts", Annals of Medicine, 38: 450-471 (2006).
Hegde, S.S. et al., "Renal dopamine and sodium excretion", Am. J. Hypertens., 3(6 Pt 2): 78S-81S (1990) [Abstract only].
Hegde, S.S. et al., "Evidence from Functional and Autoradiographic Studies for the Presence of Tubular Dopamine-1 Receptors and Their Involvement in the Renal Effects of Fenoldopam", J. Pharmacol. Exp. Ther., 251(3): 1237-45 (1989).
Clark, K.L. et al., "Effects of dopamine DA1-receptor blockade and angiotensin converting enzyme inhibition on the renal actions of fenoldopam in the anaesthetized dog", J. Hypertens., 9(12): 1143-50 (1991) [Abstract only].
Amenta, F., "Autoradiographic localization of dopamine DA-1 receptors in the rat renal vasculature using [3H]-SCH 23390 as a ligand", J. Auton. Pharmacol., 10: 373-383 (1990).
Roberts, D., "Summary of New Research: 2005-2006", Association of Research in Vision and Ophthalmology (ARVO), http://www.mdsupport.org/library/summary2006.html.
Thoma, K., "Simultaneous quantification of released succinic acid and a weakly basic drug compound in dissolution media", Eur. J. Pharm. Biopharm., 46(2): 183-90 (1998).
Brooks, D.P. et al., "Identification of Fenoldopam Prodrugs with Prolonged Renal Vasodilator Activity", J. Pharmacol. Exp. Ther., 254(3): 1084-9 (1990).
Carey, Robert M. et al., "Selective Peripheral Dopamine-1 Receptor Stimulation with Fenoldopam in Human Essential Hypertension", J. Clin. Invest., 74: 2198-2207 (1984).
Weinstock, Joseph et al., The Chemistry and Pharmacology of 3-Benzazepine Derivatives, Drugs of the Future, 10: 645-697 (1985).
Mogk, L.G. et al., "The Impact of Drug vs. Wet Macular Degeneration", ARVO 2008, Abstract, Program 4473, Poster D1064.
Doukas, John et al., "Topical Administration of a Multi-Targeted Kinase Inhibitor Suppresses Choroidal and Neovascularization and Retinal Edema", J. Cell Physiol., 216(1): 29-37 (2008).
Myles, Marvin E. et al., "Recent progress in ocular drug delivery for posterior segment disease: Emphasis on transscleral iontophoresis", Adv. Drug Deliv. Rev.,57(14): 2063-79 (2005).
Izumi-Nagai, K. et al., "Inhiibtion of Choroidal Neovascularization with an Anti-Inflammatory Carotenoid Astaxanthin", Investigative Ophthalmology and Visual Science, 49: 1679-1685 (2008).

(Continued)

*Primary Examiner* — Brenda Coleman
(74) *Attorney, Agent, or Firm* — Patrick J. Hagan; Dann, Dorfman, Herrell and Skillman, P.C.

(57) ABSTRACT

Methods and compounds are disclosed for treating dry age-related macular degeneration, and preventing or delaying the onset of wet age-related macular degeneration.

7 Claims, 3 Drawing Sheets

(56) References Cited

OTHER PUBLICATIONS

Venkatesh, Gopi M., "Development of Controlled-Release SK&F 82526-J Buffer Bead Formulations with Tartaric Acid as the Buffer", Pharm. Dev. Technol., 3(4): 477-85 (1998).

Bone, Richard A., Lutein and Zeaxathin Dietary Supplements Raise Macular Pigment Density and Serum Concentrations of these Carotenoids in Humans, J. Nutr., 133: 992-998 (2003).

Rattner, A. et al., "Macular degeneration: recent advanced and therapeutic opportunities", Nat. Rev. Neurosci., 7 (11): 860-72 (2006).

Jager, Rama D. et al., "Age-Related Macular Degeneration", N. Engl. J. Med., 358: 2606-17 (2008).

Edelhauser, Henry F. et al., "Drug Delivery to Posterior Intraocular Tissues: Third Annual ARVO/Pfizer Ophthalmics Research Institute Conference", Investigative Ophthalmology & Visual Science, 49(11): 4712-20 (2008).

Kinter, Lewis B. et al., "Characterization of the Hemodynamic Activities of Fenoldopam and Its Enantiomers in the Dog", Chirality, 2: 219-225 (1990).

Hammond, Billy R. et al., "The Age-Related Eye Disease Study (AREDS)", Nutrition Rev., 60(9): 283-288 (2002).

Reference 58/6320-R2-Rev., Abbott Laboratories 2000, pp. 1-10.

TREATMENT OF AGE-RELATED MACULAR DEGENERATION

CROSS-REFERENCE TO RELATED APPLICATIONS

The present application is a continuation-in-part of International Patent Application No. PCT/US2008/065212, filed May 30, 2008, which claims the benefit of U.S. Provisional Patent Application No. 60/941,106, filed May 31, 2007 and U.S. Provisional Patent Application No. 60/968,195, filed Aug. 27, 2007, the entire disclosures of which are incorporated by reference herein.

BACKGROUND OF THE INVENTION

Age-related macular degeneration (AMD) is the leading cause of legal blindness among people over 65. In industrial countries at least one third of persons over 75 have clinical signs of the disease (21). There are two distinct forms of AMD, known as "wet AMD" and "dry AMD". The characteristics of each are described hereinbelow. The only current treatment for dry AMD is dietary antioxidant and mineral supplements. Although there are several current therapies for the more advanced wet form, the only current treatment for dry AMD is daily oral administration of a mixture of antioxidants, vitamins, and metals. This delays progression of dry AMD and slows conversion of dry to wet AMD in about 25% of patients (1, 2, 3). Age-related macular degeneration most often presents first as the dry form that advances to the wet form in 10-15% of the patients. More serious vision loss is associated with the wet form, but up to 20% of legal blindness is due to the dry form.

The dry form of AMD is characterized by macular drusen which are pigmented areas containing dead cells and metabolic products that distort the retina and eventually cause loss of acute vision (4). The wet form is characterized by new blood vessel growth into the retina and subsequent leakage causing catastrophic damage and resulting in severe vision loss.

The retina is a highly metabolizing tissue and requires a high choroidal blood flow to provide oxygen and remove metabolites and dead cells. The necessary blood circulates in the capillaries of the choroid layer of the eye between the retina and sclera and supplies oxygen and nutrients to the reticular pigment epithelium (RPE) and the photoreceptors of the retina. On a weight basis the retina is the most oxygen utilizing tissue in the body with a relative oxygen consumption 50% greater than the brain or kidneys (32). Most of the oxygen is used in the photoreceptors, and thus the RPE and the retina are subjected to the brutal combination of 'toxic oxygen' and UV radiation. One function of the RPE is to each day degrade and dispose of 10% of the outer segments of the photoreceptors. The metabolic products and non-recycled degradation products are removed by transfer to blood in the choroidal capillaries.

Drusen, which are the tiny yellow or white accumulations of extracellular material that build up in Bruch's membrane of the eye, are normal with advancing age, and most people over 40 have some hard drusen. However, the presence of larger and more numerous drusen in the macula is a common early sign of AMD and are indicators of increased risk of the complications of AMD. Drusen in the area of the macula interfere with vision by interfering with the light path thus preventing sharp focus on the macular portion of the retina necessary to obtain good visual acuity. An important factor in the formation of drusen is poor blood circulation in the choroid due to constriction and hardening of the capillaries. This allows dead cells and toxic metabolites to accumulate.

The landmark study by the AREDS group found that subjects at high risk for developing advanced stages of AMD reduced this risk by about 25% when treated with a combination of antioxidants (vitamin C, Vitamin E, and beta-carotene/Vitamin A) and minerals (zinc and copper) (3). It also found that the use of this dietary supplement also reduced the risk of central vision loss by 19%. The trial included 3640 participants who had at least early stage AMD. The use of beta-carotene by smokers, or even former smokers, led to an increased risk of cancer. New formulations have been developed in which the beta-carotene has been replaced by a mixture of lutein and zeaxanthin, or lutein alone. These are carotinoids similar to beta-carotene, and are also potent antioxidants (28, 29).

SUMMARY OF THE INVENTION

The present invention provides a method and compounds to treat dry AMD, the prevalent form of AMD, and thereby prevent its progression. This objective is achieved in accordance with the present invention by administration of a dopamine agonist, preferably fenoldopam, a fenoldopam prodrug or a pharmaceutically acceptable salt of either of them in monotherapy, or in combination with at least one antioxidant and/or mineral supplement, for the treatment of dry AMD. The method and compounds of the invention are effective for slowing or preventing the onset of wet AMD in those patients who, because they have many drusen, are predicted to have a high risk of developing wet AMD.

DETAILED DESCRIPTION OF THE INVENTION

Figure 1:
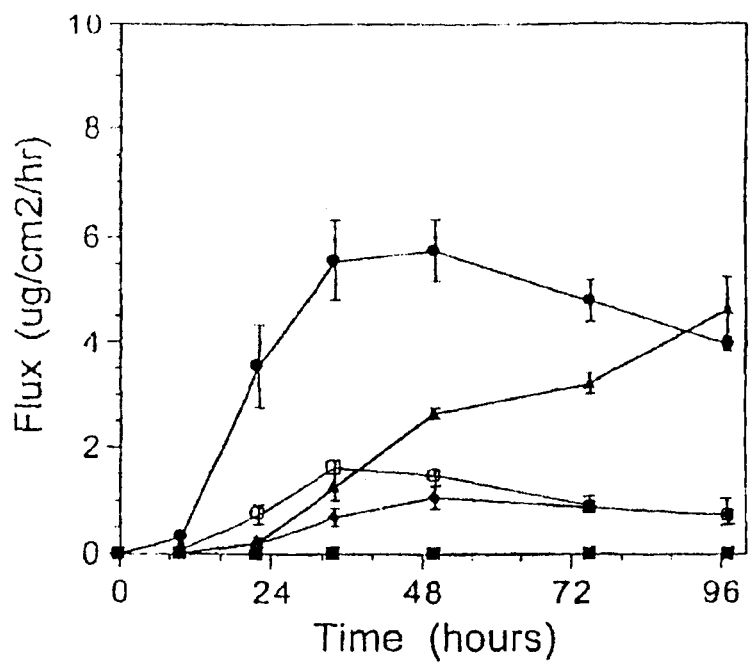
FIG. 1 is a graphical representation of a typical flux rate versus time experiment to evaluate transdermal flux through cadaver human epidermis in ug/cm$^2$ of fenoldopam mesylate using various permeability enhancers (-■- control; -●- Cla/L-dea, 20/15; -▲- Gml/Ml/Pvp, 20/12/16; Laureth-2; -♦-; and Laureth-4, -□-).

The retina is a highly metabolizing tissue and requires a high choroidal blood flow to provide oxygen and remove metabolites and dead cells. The necessary blood circulates in the capillaries of the choroid layer of the eye between the retina and sclera. In AMD, the choroidal blood flow is lower than normal. The choroid is rich in D1/5 receptors, and treatment of both animals and humans with dopamine causes an increase in choroidal blood flow (5, 6). In anesthetized rabbits dopamine caused choroidal vasodilation that was blocked by SCH-23390, a D1/5 antagonist. SKF-38393, a benzodiazepine similar to fenoldopam (SKF R-82526), and also a D1/5 agonist, caused a similar vasodilation (6). This showed that the vasodilation is caused by a D1/D5 receptor mediated mechanism. This is analogous to the renal vasodilation seen with SKF 38393 and with fenoldopam (24). This indicates that a suitable DA 1/5 agonist that could be delivered to the choroid without entering the CNS or causing hypotension could be a valuable agent for preventing or inhibiting the progression of macular degeneration.

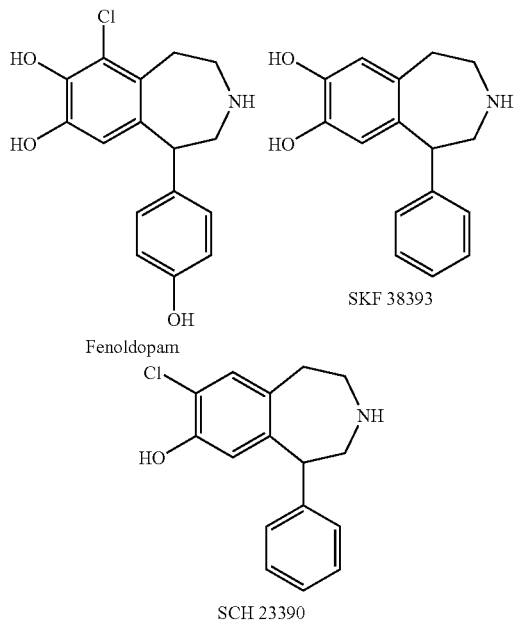

Fenoldopam

SKF 38393

SCH 23390

Fenoldopam (18) and SKF 38393 are well known DA1/5 dopamine receptor agonists while SCH 23390 is a DA 1/5 dopamine receptor antagonist (20). Pharmacologically the major differences between fenoldopam and SKF 38393 are that fenoldopam is more potent and does not cross the blood-brain barrier. Both are racemic, and the activity is carried by the R-enantiomer. Fenoldopam has been investigated extensively as a renal vasodilator and as an antihypertensive, both intravenously and orally. On intravenous dosing, at the lowest active doses the only activity seen is natriuresis (7). As the dose is raised, renal vasodilation occurs, and at higher doses, systemic hypotension develops (8, 9). It has been shown that the DA1 receptor density is higher in the proximal cortical tubules responsible for the natriuresis than in the intrarenal arteries (10), thus indicating that receptor density as well as agonist concentration determines the pharmacological expression of receptor stimulation. If the density of DA1 receptors in the choroid is sufficiently high, fenoldopam would increase choroidal blood flow without causing significant changes in blood pressure (5).

It has been shown in both animals and humans that dopamine at low doses increases choroidal blood flow by a DA1/5 mechanism. Dopamine may exert its action not only on the choroid capillaries but also on the posterior ciliaries in the cones of fat surrounding the optic nerve and cushioning the eye. Dopamine is not useful in the treatment of AMD because it is short acting and has adrenergic amine effects in addition to its dopaminergic effects. Desirable special properties of a useful dopamine agonist for treatment of dry AMD are: highly selective as a DA1/5 agonist with no significant D2 activity, no significant other catechol amine activity, does not cross the blood-brain barrier, has no significant effect on heart rate or systemic blood pressure at the doses used to increase choroidal blood flow, and has the ability to increase choroidal blood flow over a useful period of time.

Fenoldopam possesses desirable properties as a dopamine agonist for increasing choroidal blood flow because it is very selective as a DA1/5 agent, is very potent, and does not cross the blood-brain barrier which would give CNS effects (20). Previous research has demonstrated that it does not have limiting short-term toxicity in animals or humans as demonstrated in oral four-week studies in humans (19). Fenoldopam's physiological effects are dose related dependent on the site of action. In the kidney at lowest intravenous doses only diuresis is observed. At higher doses renal blood flow is increased. At still higher doses systemic hypotension occurs as other vascular beds become involved. This may be a function of receptor density as well as response of the tissue to dopaminergic stimulation. The choroid has a high density of DA1/5 receptors that bind dopamine, indicating that the choroidal capillaries might resemble renal capillaries in this manner. Low doses of fenoldopam have been shown to induce renal vasodilation without causing systemic hypotension indicating that similar doses of fenoldopam would similarly increase choroidal blood flow without inducing systemic hypotension. Racemic fenoldopam is currently used as the mesylate (methane sulfonate salt) in intravenous solution (27) as an in hospital hypotensive agent. It exists as two isomers, the R isomer which is responsible for the dopaminergic activity, and the S isomer which has no significant dopaminergic activity.

In addition, a synergistic relationship would be expected to exist with the combination of a DA1/5 agonist that increases choroidal blood flow and an anti-oxidant/mineral supplement. The ingredients of the antioxidant supplement taken orally are carried to the retina by the choroidal blood flow. In AMD the choroidal blood flow is below normal and therefore higher blood levels and/or longer exposure times are needed than if the blood flow was normal. In parts of the retina near areas of low blood flow the ingredients of the supplement may never reach the concentration necessary for a therapeutic effect. Co-administration of fenoldopam and the anti-oxidant/mineral supplement would enhance delivery of the supplement to all parts of the retina including those areas which have only a few functioning choroidal capillaries.

Access to the choroid other than via the blood is difficult. The eye is composed of three major anatomic compartments, the anterior chamber, posterior chamber, and vitreous cavity, that have limited physiological interaction with each other. The retina is located in back of the vitreous cavity, and is protected from the outside by the sclera which is the white, tough, impermeable wall of the eye. Thus most drugs cannot be delivered to the choroid by eyedrops or a depot immediately outside the eye. However, some drugs have been delivered to the retina (and thus to the choroid) by injection into the vitreous chamber of the eye (11), mostly in a delayed release media. Also, some drugs have been delivered to the retina (and thus to the choroid) by trans scleral transport (eye drops) (22, 23) and this would be a convenient and effective dosage route. In some cases the drug has been converted to a prodrug to facilitate this transport. Choroidal blood flow is the usual method of carrying substances to the choroid. An orally absorbed drug can be administered in capsule or tablet form designed for either immediate or sustained release. A sustained release prodrug form would prolong exposure time for a short acting drug.

A conventional dosage form is a low dose fenoldopam tablet with either rapid or slow release properties. It is important to maintain a low blood level of fenoldopam because many of the patients receiving it are elderly and on various other drugs, and adding a potent antihypertensive agent would be a potential complication that would preferably be avoided. As used herein, the term "patient" refers to animals, including mammals, preferably humans.

Fenoldopam is presently marketed only as a solution for intravenous injection which must be diluted before use (27). However, fenoldopam has been studied as an oral formulation at hypotensive doses for periods of up to four weeks (19).

Fenoldopam is a catechol amine, and as such has a short duration of action. The duration of action may be prolonged by the use of a sustained release preparation. The feasibility of such a dose formulation was suggested by a pharmacokinetic study and by the preparation of slow-releasing fenoldopam formulations (12, 26). The balanced drug release and clearance would prevent an excessively high peak blood concentration as is typical with standard formulations when long duration of action is desired.

Another drug delivery option would be transdermal transport by means of a patch. This also has the advantage of avoiding peak effects which can occur on oral dosing. Several such systems specifically for fenoldopam have been patented. Such patches are currently successfully used to deliver drugs such as steroids, scopolamine for motion sickness, nitroglycerine for angina, and fentanyl for intractable pain. Three patents have issued which relate to patches that release fenoldopam at a constant rate for up to 96 hours (13, 14, 15).

FIG. 1 shows the rate at which fenoldopam is transferred from a transdermal patch, including various permeation enhancers, through human cadaver skin. The enhancers identified in FIG. 1 are caproyl lactic acid and luramide diethanolamine, used in a ratio of 20/15 (-●-); glycerol monolaurate/myristyl lactate/polyvinyl pyrrolidone, used in a ratio of 20/12/16 (-▲-); polyethylene glycol (PEG)-2 laurylether (-♦-); and PEG-4 laurylether (-□-).

A third option would be use of a prodrug. SK&F 105058, a triprotected compound, may be suitable for use as a prodrug for fenoldopam. It was shown to release fenoldopam slowly after oral absorption. Fenoldopam blood level and renal vasodilator effect was studied in the dog as a function of time after oral dosing of several prodrugs. SK&F 105058 was the most successful (16, 17). However other prodrugs such as esters, carbonates, and carbamates on the benzazepine nitrogen could be used, if desired. The last mentioned prodrugs would have the partial structure

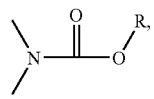

R=lower alkyl, a representative example being

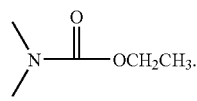

If the prodrug is too lipophilic it may cross the blood-brain barrier, so a balance must be achieved. The prodrug could be designed to enhance absorption, or it could be designed to slowly release the active parent after absorption.

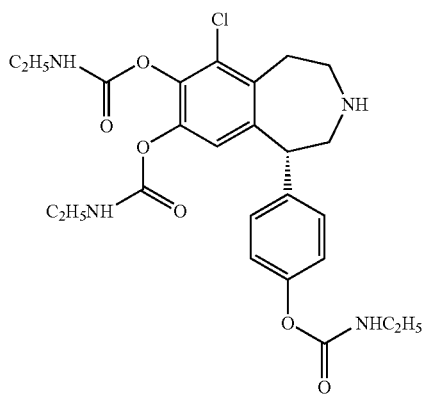

SKF 105058

Figure 2A:
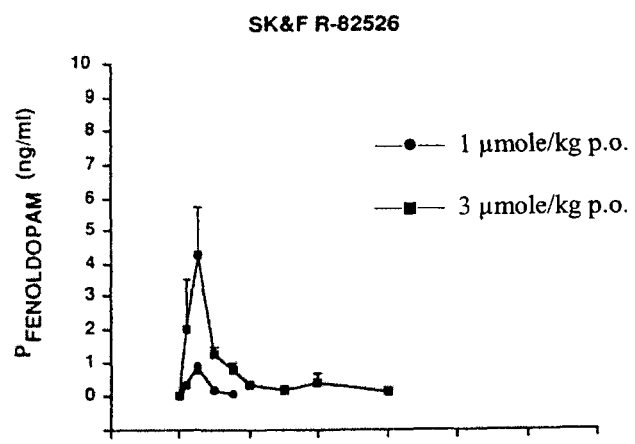
FIG. 2 is a set of graphical representations of the results of time course experiments showing (A) the effect of oral administration of R-fenoldopam (1 and 3 micromoles per kilogram in conscious dogs) on plasma fenoldopam concentration (ng/ml) and (B) renal blood flow (RBF, % change). Baseline RBF=56+/−7 ml/min. Values are mean+/−S.E. (16).
Figure 2B:
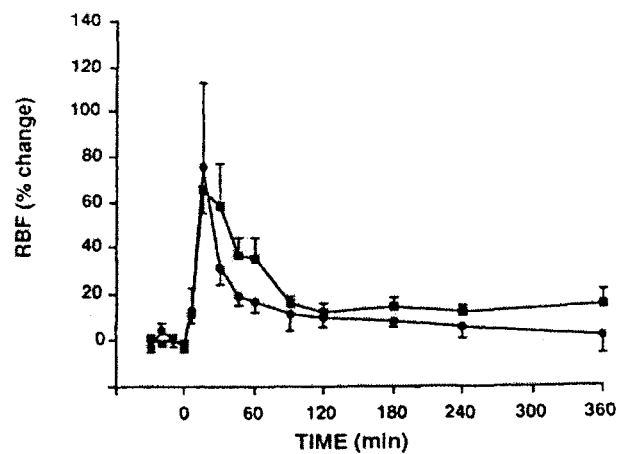
Figure 3A:
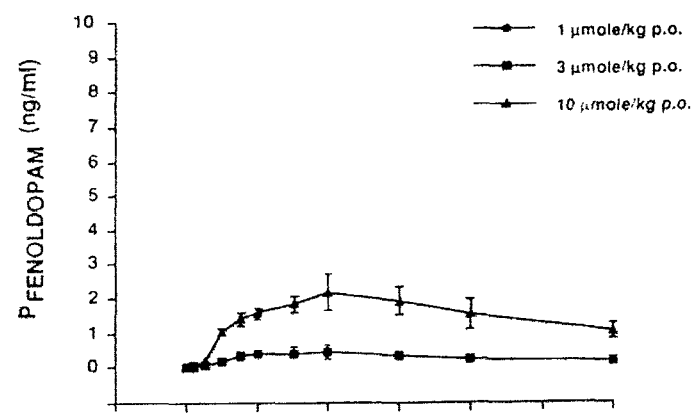
FIG. 3 is a set of graphical representations of the results of time course experiments showing (A) the effect of oral administration to conscious dogs of SKF R-105058 on plasma fenoldopam concentration; and (B) RBF (16). Baseline renal blood flow=49+1−1 ml/min. Values are ±S.E.
Figure 3B:
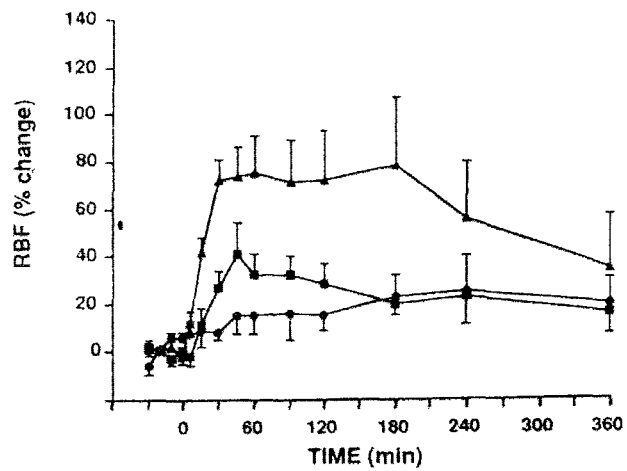

Plasma fenoldopam levels and percent increase of renal blood flow (RBF) on oral dosing in dogs are shown in FIGS. 2a and 2b. Fenoldopam on oral dosing rapidly gives high drug blood level and concomitant increase in renal blood flow, but both are of relatively short duration. In contrast, the prodrug SKF 10508 gives a more gradual increase of drug blood level, but the increase in renal blood flow is rapid and sustained for a much longer time (greater than 6 hours), as shown in FIGS. 3A and 3B. It should be noted that in the case of administration of the racemic form of fenoldopam or its prodrugs, e.g., SK&F 105058, twice the dose shown in FIGS. 2 and 3 would be required to obtain the renal blood flow increases produced by the R-enantiomers (16).

The use of a trans scleral dosage route would require a lipophilic drug form that promotes absorption to the posterior ciliaries imbedded in the cones of fat. However, fenoldopam itself is not lipophilic so a suitable prodrug approach for this would be to mask the aromatic 7,8,4'-hydroxyl groups of fenoldopam as esters of aromatic and aliphatic acids such as benzoic acid and isobutyric acid. These would be rapidly cleaved after absorption.

The oral dose required to obtain the desired therapeutic effect, i.e., treatment or prevention of AMD, should be sufficient to provide a sustained drug plasma level for many hours, but not necessarily for 24 hours per day. An analogy would be the widespread use of short acting diuretics such as furosemide. Useful drug plasma levels of R-fenoldopam are 0.25 to 10 ng/ml, a preferred drug plasma level of 0.25 to 5 ng/ml, and a most preferred level of 0.25 to 2.5 ng/ml. If racemic fenoldopam is used, the drug levels would be twice of those stated above. SK&F 105058, the triprotected compound, may be suitable for use as a prodrug for fenoldopam.

A consequence of increasing choroidal blood flow is not only to increase delivery of oxygen and nutrients to the retina, but also to increase the delivery of systemically dosed pharmaceuticals used to treat eye diseases whose site of action is in the retina, choroid or posterior chamber of the eye. This is especially relevant to AMD where one factor in the disease is reduced choroidal blood flow. The combined use of fenoldopam and systemically or topically dosed drugs for the treatment of wet and dry AMD and glaucoma should enhance delivery of these drugs to their site of action. Useful delivery forms for this use include eye drops and eye ointments.

The landmark study by the AREDS group found that subjects at high risk for developing advanced stages of AMD reduced this risk by about 25% when treated with a combination of antioxidants (vitamin C, Vitamin E, and beta-carotene) and minerals (zinc and copper). They also found that the use of this dietary supplement also reduces the risk of central vision loss by 19%. The trial included 3640 participants who had at least early stage AMD. Daily doses of antioxidants and zinc of the original AREDS supplements were 500 milligrams of vitamin C; 400 international units of vitamin E; 15 milligrams of beta-carotene; 80 milligrams of zinc as zinc oxide; and two milligrams of copper as cupric oxide. The purpose of the copper oxide is to counteract the tendency of zinc to inhibit copper absorption. Beta carotene, a carotinoid, is an important part of the supplement because it is a potent antioxidant. It has been demonstrated to quench singlet oxygen ($^1O_2$), scavenge peroxyl radicals and inhibit lipid peroxidation. However, it was found that smokers, and even former smokers, who took high doses of beta carotene had an increased risk of cancer. With this in mind, formulations of the mixture in which beta carotene was replaced by lutein, or a mixture of lutein and zeaxanthin were developed and are currently marketed for treatment of AMD (29, 30).

Beta-carotene, lutein, zeaxanthin, and meso-zeaxanthin are members of the carotenoid family (29, 30, 31). They are natural fat-soluble yellowish pigments found in some plants, algae and photosynthetic bacteria. They serve as accessory light-gathering pigments and to protect these organisms against the toxic effects of ultra-violet radiation and oxygen. The structures of beta carotene, letein, zeaxanthin and astaxanthin are shown below. Astixanthin is a powerful free radical scavenger anti-oxidant increasingly recognized for its disease-fighting properties. It is used as a dietary supplement and also used in cosmetics because of its ability to protect against UV radiation.

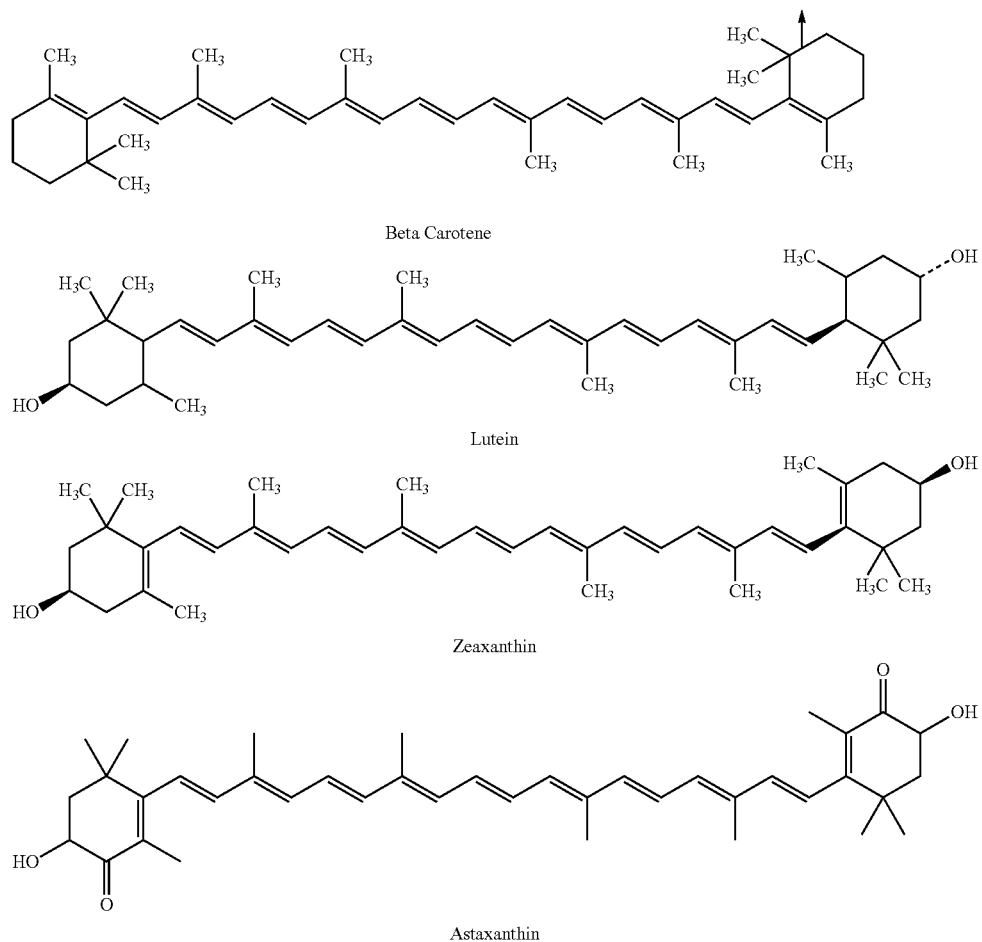

Beta Carotene

Lutein

Zeaxanthin

Astaxanthin

Lutein, zeaxanthin and meso-xanthin which are naturally present in the macula of the human retina, filter out potentially phototoxic blue light and near-ultraviolet radiation from the macula (28). The protective effect is also in part due to the reactive oxygen species quenching ability of these carotenoids. Furthermore, lutein and zeaxanthin are more stable to decomposition by oxidants such as those arising from the reaction of light with oxygen than are other carotenoids such as beta-carotene. Zeaxanthin is the predominant pigment in the fovea, the region at the center of the macula. The quantity of zeaxanthin gradually decreases and the quantity of lutein increases in the region surrounding the fovea, and lutein is the predominant pigment at the outermost periphery of the macula. Zeaxanthin, which is fully conjugated (lutein is not), may offer somewhat better protection than lutein against phototoxic damage caused by blue and near-ultraviolet light radiation. These carotioids are orally absorbed and the macular density of these pigments correlates with serum concentration. Astaxanthin, a more potent antioxidant than other carotenoids has been used as a food supplement, has been shown to inhibit choroidal neovascularization (25). The occurrence of zeaxanthin, meso-zeaxanthin and lutein in the retina, but with different spatial distribution, suggests that a mixture with or without beta-carotene, might exert a more efficacious antioxidant activity over the entire macula than lutein by itself.

The ingredients of AREDS type supplements are delivered to the macula by transportation from the capillaries of the choroid. In AMD the choroidal blood flow is lower than normal and the transport of members of the antioxidant formula into the macula may not be maximal. Increasing choroidal blood flow by co-administration of fenoldopam may enhance transport of members of the antioxidant formula into the macula, especially in areas of poor blood flow susceptible to drusen formation. This could be accomplished by independent dosing with separate dosage forms, or preferably by incorporating fenoldopam and the antioxidant mixture into one dosage form. Since the beneficial effects of the antioxidant mixture and a D1/D5 agonist are due to different mechanisms, an additive or even a synergistic effect may be seen.

A dosage form can contain both fenoldopam and one or more members of the antioxidant-vitamin-mineral mixture. Such a dosage form could release all the components normally, or it could release one or more of the components over an extended period of time.

Aromatic or heteroaromatic fenoldopam esters for enhancing trans scleral topical absorption are shown in Structure I.

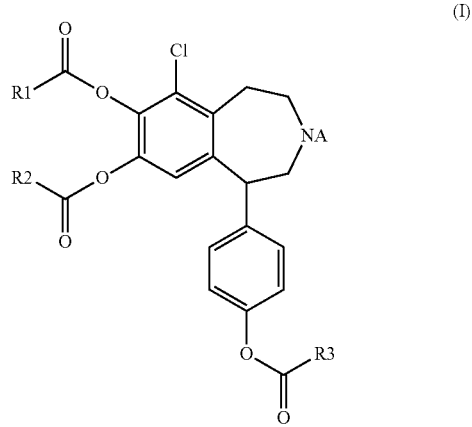

(I)

either as the racemate or the R-enantiomer, and one or two of $R_1$ (C=O)—, $R_2$ (C=O)—, $R_3$ (C=O)— may be replaced by H, wherein $R_1$, $R_2$ and $R_3$ may be the same or different and represent

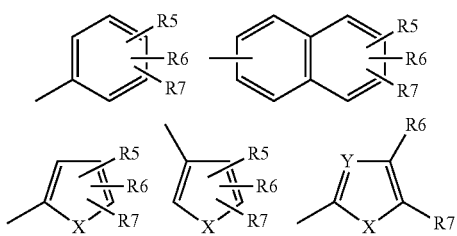

-continued

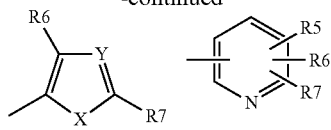

wherein X and Y are independently S, O, N, $NR_8$

A represents H or —(C=O)$OR_B$, and when A is H, the compound may form a pharmaceutically acceptable salt of an acid such as hydrochloric, hydrobromic, methanesulfonic, alkyl sulfonic acid of 1 to 4 carbon atoms branched or unbranched, arylsulfonic, aryl or heteroaryl carboxylic acid;

$R_5$, $R_6$, $R_7$ independently represent H, F, Cl, $CF_3$, Br, I, alkyl of 1 to 6 carbons branched or unbranched, or chains of 3 to 5 atoms including C, N, S, O, with or without bonds double, with or without attached $R_5$, $R_6$, $R_7$ groups, which may comprise two adjacent $R_5$, $R_6$, or $R_7$ groups to form a closed ring; and $R_8$ is an alkyl group of 1-10 carbon atoms which may be branched or straight chain.

The pharmaceutically acceptable acid salts may also include an alkanoic acid of 2-6 carbons unbranched or branched.

In particular embodiments, $R_1$, $R_2$, $R_3$ in the compounds of Structure I may represent a phenyl or naphthyl (1- or 2-) moiety, substituted with one or more of the $R_5$, $R_6$, $R_7$ groups.

A particular species which may be used in the practice of this invention is 6-Chloro-7,8-dibenzoyloxy-1-(p-benzoyloxyphenyl)-2,3,4,5-tetrahydro-1H-3-benzazepine hydrochloride.

To prepare the compounds of Structure I where each $R_1$, $R_2$ and $R_3$ is aryl or heteroaryl, a fenoldopam salt, such as the hydrochloride, is suspended in trifluoroacetic acid at ambient temperature with 3 equivalents of the appropriate acid halide or anhydride such as benzoyl chloride, refluxed for several hours, and allowed to stand with stirring for an additional 16 hours. Evaporation of the solvent under vacuum and recrystallization gives the fenoldopam triester as the hydrochloride. In some cases it may be necessary to heat the reaction mixture longer to drive the reaction to completion.

Biological Testing

An animal model of dry AMD (33) uses mice which have had a ribozyme that targets the protective enzyme manganese superoxide dismutase (MnSOD) injected beneath the retina. The ribozyme (AAV-Rz 432) method allows site specific somatic knockdown of SOD 2 expression in normal adult tissue so that the lesion is only in the injected eye and the rest of the body is unaffected. Thus the other eye can act as a control. This protocol has been shown to induce in the eyes of the mice after a single subretinal injection of the ribozyme many of the abnormalities seen in the eyes of patients with AMD, with the most severe changes seen 120 days post injection. The surrogate markers for protection from reactive oxygen and nitrogen species damage are examined by electroretinography (ERG) and morphometry.

Analysis of Retinal Structure and Function in Living Mice:

Full field ERG analysis (34) may be used to assess the loss of rod and cone function, measuring a-wave and b-wave amplitudes in dark adapted and light adapted mice. Digital fundus imaging with a Micron II retinal imaging microscope from Phoenix Research Laboratories may be used to monitor atrophic changes in the retinal pigment epithelium (RPE).

Morphometry:

Light microscopy may be used to qualitatively assess damage to the photoreceptors and RPE, to look for evidence of choroidal neovascularization and to measure changes in the thickness of Bruch's membrane. Retinal degeneration is determinable morphometrically by measuring the thickness of the outer nuclear layer and rod outer segments (35). Statistical analysis may be performed by t-test for paired samples for disease induced by the AAV-ribozyme.

In a typical study, adult mice are treated subretinally in one eye with the ribozyme AAV-RZ 432 (33). Several groups are each treated daily with the chosen dose of fenoldopam mesylate by gavage, and individuals from each group are examined by electroretinography at intervals during the 120 day course of the experiment. At the end of 120 days the mice are sacrificed and their eyes examined for the surrogate markers in each case comparing the ribozyme injected eye with the ribozyme uninfected eye.

In order to study synergism of fenoldopam and the ARADS mixture, ribozyme injected groups may be treated by gavage with the same doses of fenoldopam used above and also with feed supplemented at species adjusted doses to mimic the AREDS mixture with lutein, zeoxanthin, vitamins C and E, zinc, and copper. In addition, a group of mice may be treated with only the ARADS mixture. Control groups include mice treated the ribozyme AAV-RZ 432 who receive neither drug nor feed additive, and mice who are not treated with the ribozyme and are not receiving drug or feed supplement. Each of these groups is examined for the surrogate markers.

A number of patent and non-patent publications are cited throughout the foregoing specification in order to describe the state-of-the-art to which this invention pertains. The entire disclosure of each of these publications is incorporated by reference herein.

While certain embodiments of the present invention have been described and/or exemplified above, various other embodiments will be apparent to those skilled in the art from the foregoing specification. The present invention is, therefore, not limited to the particular embodiments described and/or exemplified, but is capable of considerable variation and modification without departure from the scope of the appended claims. Furthermore, the transitional terms "comprising", "consisting essentially of" and "consisting of" define the scope of the appended claims, in original and amended form, with respect to what unrecited additional claim elements or steps, if any, are excluded from the scope of the claims. The term "comprising" is intended to be inclusive or open-ended and does not exclude additional, unrecited elements, methods step or materials. The phrase "consisting of" excludes any element, step or material other than those specified in the claim, and, in the latter instance, impurities ordinarily associated with the specified materials. The phrase "consisting essentially of" limits the scope of a claim to the specified elements, steps or materials and those that do not materially affect the basic and novel characteristic(s) of the claimed invention. All compositions or formulations identified herein can, in alternate embodiments, be more specifically defined by any of the transitional phases "comprising", "consisting essentially of" and "consisting of".

REFERENCES

1. Gehrs K M, Anderson D H et al, Age-related macular degeneration-emerging pathogenic and therapeutic concepts, Annals of Medicine, 2006, 38, 459-471.
2. ARVO 2002. Report of the 2002 meeting of the Association for Research in Vision and Opthalmology.
3. Age-Related Eye Disease Study Research Group, A randomized, placebo-controlled, clinical trial of high dose supplementation with vitamins C and E, beta carotene, and zinc for age-related macular degeneration and vision loss: AREDS report no. 8. Arch Opthalmol. 2001, 119, 1417-1436.
4. Macular Degeneration Foundation, Chapter 3. http:eyesight.org.
5. Huemer K H, Zawinka et al, Effects of dopamine on retinal and choroidal blood flow parameters in humans, Br J Opthalmol, published online 23 Mar. 2007.
6. Reitsamer H A, Zawinka, and Branka M, Dopaminergic vasodilation in the choroidal circulatin by D1/D5 Receptor Activation, Investigative Opthalmology and Visual Science, 2004, 45, 900-905.
7. Hegde S S, Lokhandwala M F, Renal dopamine and sodium excretion, Am J Hypertension, 1990, 3 (6 pt 2) 78S-81S,
8. Hegde S S, Ricci A et al, Evidence from functional and autoradiographic studies for the presence of tubular dopamine-1 receptors and their involvement in the renal effects of fenoldopam, J Pharmacol Exp Ther. 1989, 251 (3):1237-45.
9. Clark K L, Hilditech A et al, Effects of dopamine DA1-receptor blockade and angiotensin converting enzyme inhibition on the renal actions of fenoldopam in the anaesthetized dog, J. Hypertens. 1991, 9 (12):1143-50.
10. Amenta F and Ricci A, Autoradiographic localization of dopamine DA-1 receptors in the rat renal vasculature using [3H]-SCH 23390 as a ligand, J Auton Pharmacol. 1990, 10 (6), 373-83.
11. Roberts D, Summary of new research, Association of Research in Vision and Opthalmology (ARVO), http://www.mdsupport.org/library/summary2006/html.
12. Thoma K, Ziegler I, Simultaneous quantification of released succinic acid and a weakly basic drug compound in dissolution media. Eur J Pharm Biopharm. 1998, 46 (2), 183-90.
13. U.S. Pat. No. 6,238,693. Transdermal administration of fenoldolpam, May 29, 2001. Luther R R, McGuire D, Mathur V, Ellis D J, Assignee: Elan Pharmaceuticals, Inc.
14. U.S. Pat. No. 6,960,353. Formulations for the transdermal administration of fenoldopam, Nov. 1, 2005. van Osdol W W, Crisologo N M, Yum, S I, Assignee: Alza Corporation.
15. U.S. Pat. No. 6,699,497. Formulations for the transdermal administration of fenoldopam, Nov. 1, 2005. van Osdol W W, Crisologo N M, Nieves M, Yum S I, Assignee: Alza Corporation.
16. Brooks D P, DePalma P D, Identification of fenoldopam prodrugs with prolonged renal vasodilator activity, J Pharmacol Exp Ther. 1990, 254(3), 1084-9.
17. Gaitanopoulos, D, Mico B, Weinstock J, Preparation of fenoldopam carbamates as antihypertensive agents, U.S. Pat. No. 4,861,771 (1989).
18. US Food and Drug Administration, Center for Drug Evaluation and Research, http://www.accessdata.fda.govi-scripts/cder/drugsatfda/

19. Carey R M, Stote R M et al, Selective Peripheral Dopamine Receptor Stimulation with Fenoldopam in Human Essential Hypertension, J Clin Invest. 1984, 74(6):2198-207.
20. Weinstock J, Hieble J P, and Wilson J W, The Chemistry and Pharmacology of 3-Benzazepine Derivatives, Drugs of the Future, 1985, 10, 645-697.
21. Mogk L G, Geringer C, et al, The Impact of Dry vs. Wet Macular Degeneration, ARVO 2008, Abstract, Program 4473, Poster D1064.
22. Doukas J, Mahesh S, Umeda N, Kachi S, Akiyama H, Yokoi K, Cao J, Chen Z, Dellamary L, Tam B, Racanelli-Layton A, Hood J, Martin M, Noronha G, Soll R, Campochiaro P A., Topical administration of a multi-targeted kinase inhibitor suppresses choroidal neovascularization and retinal edema, J Cell Physiol. 2008, 216(1):29-37.
23. Adv Drug Deliv Rev. 2005 Dec. 13; 57(14):2063-79, Myles M E, Neumann D M, Hill J M, Recent progress in ocular drug delivery for posterior segment disease: emphasis on transscleral iontophoresis, Recent progress in ocular drug delivery for posterior segment disease: emphasis on transscleral iontophoresis, Adv Drug Deliv Rev. 2005, 57(14), 2063-79.
24. Weinstock, J, 6-Halo-7,8-dihydroxy-1-(hydroxyphenyl)-2,3,4,5-tetrahydro-1H-3-benzazepines, U.S. Pat. No. 4,197,297 (1980).
25. Kanako Izumi-Nagai, Norihiro Nagai, Kazuhiro Ohgami, Shingo Satofuka, Yoko Ozawa, Kazuo Tsubota, Shigeaki Ohno, Yuichi Oike, and Susumu Ishida, Inhibition of Choroidal Neovascularization with an Anti-Inflammatory Carotenoid Astaxanthin, Investigative Opthalmology and Visual Science. 2008, 49, 1679-1685.
26. Venkatesh G M, Development of controlled-release SK&F 82526-J buffer bead formulations with tartaric acid as the buffer, Pharm Dev Technol. 1998, 3(4), 477-85.
27. Physicians Desk Reference, 2003, 57, 412-414.
28. Bone R A, Landrum J T, Guerra L H, Ruiz C A, Lutein and zeaxanthin dietary supplements raise macular pigment density and serum concentrations of these carotenoids in humans. J Nutr 2003, 133, 992-998.
29. Carotenoids and Retinoids: Molecular Aspects and Health Issues. Editors Lester Packer, Ute Obermueller-Jevic, Klaus Kraemer, and Helmut Sies. AOCS Press, 2005. ISBN #1-893997-83-9
30. Carotenoids in Health and Disease. Editors Norman I. Krinsky, Susan T. Mayne, Helmut Sies. Marcel Dekker, Inc. New York, 2004. ISBN #0-8247-5416-6.
31. Carotenoids—Handbook, G. Britton, S. Liaaen-Jensen and H. Pfander (eds). Birkhauser Verlag, 2004.
32. Rattner A and Nathans J, Macular degeneration: recent advances and therapeutic opportunities. Nat Rev Neurosci. 2006, 7(11), 860-72.
33. Justilien V, Pang, J P, et al, SOD2 Knockdown Mouse Model of Early AMD, Invest Opthalmol V is Sci, 2007, 48 (10), 4407-4420.
34. Goto Y, Peachey N S, Ripps H, Naash M I. Functional abnormalities in transgenic mice expressing a mutant rhodopsin gene, Invest Opthalmol Vis Sci 1995, 36, 62-71.
35. Faktorovich E G, Steinberg R H, Yasumura D, Matthes M T, LaVail M M. Photoreceptor degeneration in inherited dystrophy delayed by the basic fibroblast growth factor, Nature 1990, 347, 83-86.

What is claimed is:
1. A compound of the formula:

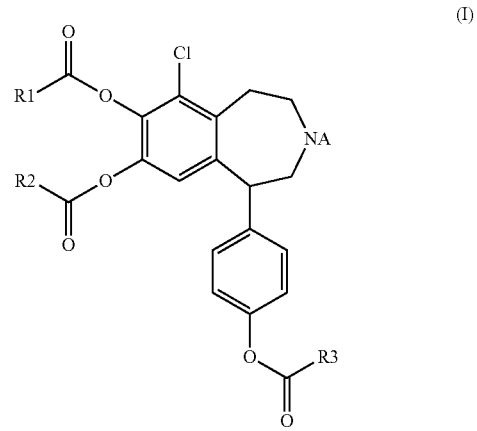

(I)

either as the racemate or the R-enantiomer,
and one or two of $R_1$ (C=O)—, $R_2$ (C=O)—, $R_3$ (C=O)— may be replaced by H, wherein $R_1$, $R_2$ and $R_3$ may be the same or different and represent

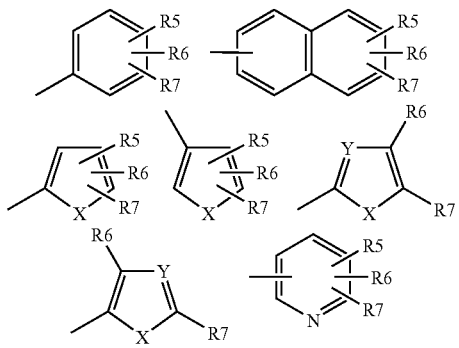

wherein X and Y are independently S, O, N, $NR_8$
A represents H or —(C=O) $OR_\beta$, and when A is H, the compound may form a pharmaceutically acceptable acid salt;
$R_5$, $R_6$, $R_7$ independently represent H, F, Cl, $CF_3$, Br, I, alkyl of 1 to 6 carbons branched or unbranched, or chains of 3 to 5 atoms including C, N, S, O, with or without bonds double, with or without attached $R_5$, $R_6$, $R_7$ groups, which may comprise two adjacent $R_5$, $R_6$, or $R_7$ groups to form a closed ring; and $R_8$ is an alkyl group of 1-10 carbon atoms which may be branched or straight chain.

2. The compound of claim 1, wherein said pharmaceutically acceptable acid salt is selected from the group consisting of a hydrochloric, hydrobromic, methanesulfonic, alkyl sulfonic acid of 1 to 4 carbon atoms branched or unbranched, arylsulfonic, aryl or heteroaryl carboxylic acid salt.

3. The compound of claim 1, wherein said pharmaceutically acceptable acid salt is a salt of an alkanoic acid of 2-6 carbons unbranched or branched.

4. The compound of claim 1 in which $R_1$, $R_2$, $R_3$ represent a phenyl or naphthyl (1- or 2-) moiety, substituted with one or more of said $R_5$, $R_6$, $R_7$ groups.

5. The compound 6-Chloro-7,8-dibenzoyloxy-1-(p-benzoyloxyphenyl)-2,3,4,5-tetrahydro-1H-3-benzazepine hydrochloride.

6. A method for treating dry age-related macular degeneration in a patient in need thereof, the method comprising administering to said patient a therapeutically effective amount of a compound as claimed in claim 1.

7. The method of claim 6, wherein the R-enantiomer of said compound is administered to said patient.

\* \* \* \* \*